(12) United States Patent
Hearn et al.

(10) Patent No.: US 10,456,539 B2
(45) Date of Patent: Oct. 29, 2019

(54) INHALER

(75) Inventors: Alex Hearn, London (GB); Iain McDerment, Royston (GB)

(73) Assignee: KIND CONSUMER LIMITED, London (GB)

( * ) Notice: Subject to any disclaimer, the term of this patent is extended or adjusted under 35 U.S.C. 154(b) by 1284 days.

(21) Appl. No.: 13/389,431

(22) PCT Filed: Aug. 6, 2010

(86) PCT No.: PCT/GB2010/001488
§ 371 (c)(1),
(2), (4) Date: Feb. 7, 2012

(87) PCT Pub. No.: WO2011/015826
PCT Pub. Date: Feb. 10, 2011

(65) Prior Publication Data
US 2012/0138054 A1 Jun. 7, 2012

(30) Foreign Application Priority Data

Aug. 7, 2009 (GB) .................................... 0913942.9
Jan. 11, 2010 (GB) .................................... 1000403.4
Feb. 8, 2010 (GB) .................................... 1002024.6

(51) Int. Cl.
*A61M 15/00* (2006.01)
*A24F 47/00* (2006.01)
(Continued)

(52) U.S. Cl.
CPC ....... *A61M 15/0093* (2014.02); *A24F 47/002* (2013.01); *A61M 15/0091* (2013.01);
(Continued)

(58) Field of Classification Search
CPC A61M 15/06; A61M 11/06; A61M 2011/002; A61M 16/18; A61M 2202/064;
(Continued)

(56) References Cited

U.S. PATENT DOCUMENTS 2,989,970 A * 6/1961 Early .................... A61M 16/00
137/505.46
3,187,748 A * 6/1965 Mitchell ........... A61M 15/0065
128/200.23
(Continued)

FOREIGN PATENT DOCUMENTS

FR 1601834 A 9/1970
WO WO 02/26300 4/2002
(Continued)

OTHER PUBLICATIONS

International search report for application No. PCT/GB2010/001488 dated Nov. 25, 2010.
(Continued)

*Primary Examiner* — Tan-Uyen T Ho
*Assistant Examiner* — Victoria Murphy
(74) *Attorney, Agent, or Firm* — Patterson + Sheridan, LLP

(57) ABSTRACT

An inhaler comprising a reservoir of an inhalable composition. A housing contains the reservoir and has an outlet end and an opposite end. A composition flow path for the flow of the composition extends from the reservoir along the flow path and out of a composition outlet at the outlet end of the housing. A flexible diaphragm within the housing defines an air flow path from an air inlet to an air outlet at the outlet end of the housing, the diaphragm extending past the air flow inlet towards the opposite end separating the air flow path on one side of the diaphragm from the remainder of the housing on the opposite side of the diaphragm. A valve element is movable with the diaphragm and biased by a biasing force into a position in which it closes the composition flow path, wherein suction on the outlet end reduces the pressure in the air flow chamber thereby lifting the valve element against the biasing force to open the composition flow path; and
(Continued)

wherein the biasing force is arranged to close the composition flow path once the suction ceases.

15 Claims, 2 Drawing Sheets

(51) Int. Cl.
  *A61M 15/06* (2006.01)
  *A61M 16/20* (2006.01)
(52) U.S. Cl.
  CPC ............ *A61M 15/06* (2013.01); *A61M 16/20* (2013.01); *A61M 2205/8225* (2013.01)
(58) Field of Classification Search
  CPC ...... A61M 15/00; A61M 15/08; A61M 16/16; A61M 16/1075; A61M 2016/109; A61M 15/0091; A61M 15/0093; A61M 16/20; A61M 2205/8225; A24F 47/002
  USPC ............ 128/202.21, 200.21, 203.12, 203.23, 128/203.16, 203.17; 131/273, 194, 271, 131/329, 330, 360
  See application file for complete search history.

(56) References Cited

U.S. PATENT DOCUMENTS

| | | | | |
|---|---|---|---|---|
| 3,456,646 A * | 7/1969 | Phillips | ............. | A61M 15/0091 128/200.23 |
| 4,054,133 A | 10/1977 | Myers | | |
| 4,393,884 A | 7/1983 | Jacobs | | |
| 4,945,931 A | 8/1990 | Gori | | |
| 4,955,371 A | 9/1990 | Zamba et al. | | |
| 4,955,372 A * | 9/1990 | Blackmer | ................ | A61D 7/04 128/203.16 |
| 5,027,808 A | 7/1991 | Rich et al. | | |
| 5,161,524 A * | 11/1992 | Evans | ................ | A61M 15/0065 128/200.24 |
| 5,297,542 A * | 3/1994 | Bacon | ................ | A61M 15/0093 128/200.14 |
| 5,447,150 A * | 9/1995 | Bacon | ................ | A61M 15/0091 128/200.14 |
| 5,507,281 A * | 4/1996 | Kuhnel | ............. | A61M 15/0065 128/203.12 |
| 5,738,087 A * | 4/1998 | King | ................. | A61M 15/0086 128/200.23 |
| 5,839,430 A * | 11/1998 | Cama | .................. | A61B 5/0871 128/200.14 |
| 6,029,661 A * | 2/2000 | Whaley | ............. | A61M 15/0065 128/203.15 |
| 6,318,366 B1 | 11/2001 | Davenport | | |
| 6,422,234 B1 * | 7/2002 | Bacon | ............... | A61M 15/0091 128/200.14 |
| 6,581,590 B1 | 6/2003 | Genova et al. | | |
| 7,168,597 B1 * | 1/2007 | Jones | ................ | A61M 15/0065 128/200.23 |
| 7,225,805 B2 * | 6/2007 | Bacon | ...................... | 128/200.23 |
| 8,671,934 B2 * | 3/2014 | Addington | ............. | A61M 11/06 128/200.21 |
| 2002/0056449 A1 * | 5/2002 | Wakefield | ......... | A61M 15/0091 128/200.23 |
| 2003/0136399 A1 * | 7/2003 | Foley | .................... | A61M 11/06 128/200.14 |
| 2004/0118396 A1 | 6/2004 | Hughes et al. | | |
| 2004/0255947 A1 * | 12/2004 | Martin | ................... | A62B 18/10 128/206.15 |
| 2005/0061327 A1 * | 3/2005 | Martin | ................... | A62B 18/10 128/206.15 |
| 2006/0231093 A1 * | 10/2006 | Burge | ............... | A61M 15/0091 128/203.15 |
| 2011/0155129 A1 * | 6/2011 | Stedman | ............. | A61M 15/009 128/200.23 |
| 2011/0315152 A1 * | 12/2011 | Hearn et al. | ................... | 131/273 |

FOREIGN PATENT DOCUMENTS

| | | |
|---|---|---|
| WO | 2002045783 A1 | 6/2002 |
| WO | 2008130813 A1 | 10/2008 |
| WO | 2010073018 A1 | 7/2010 |

OTHER PUBLICATIONS

GB examination report for application No. GB1106397.1 dated May 19, 2011.
GB search report for applicaqtion No. GB1000403.4 dated Apr. 30, 2010.

\* cited by examiner

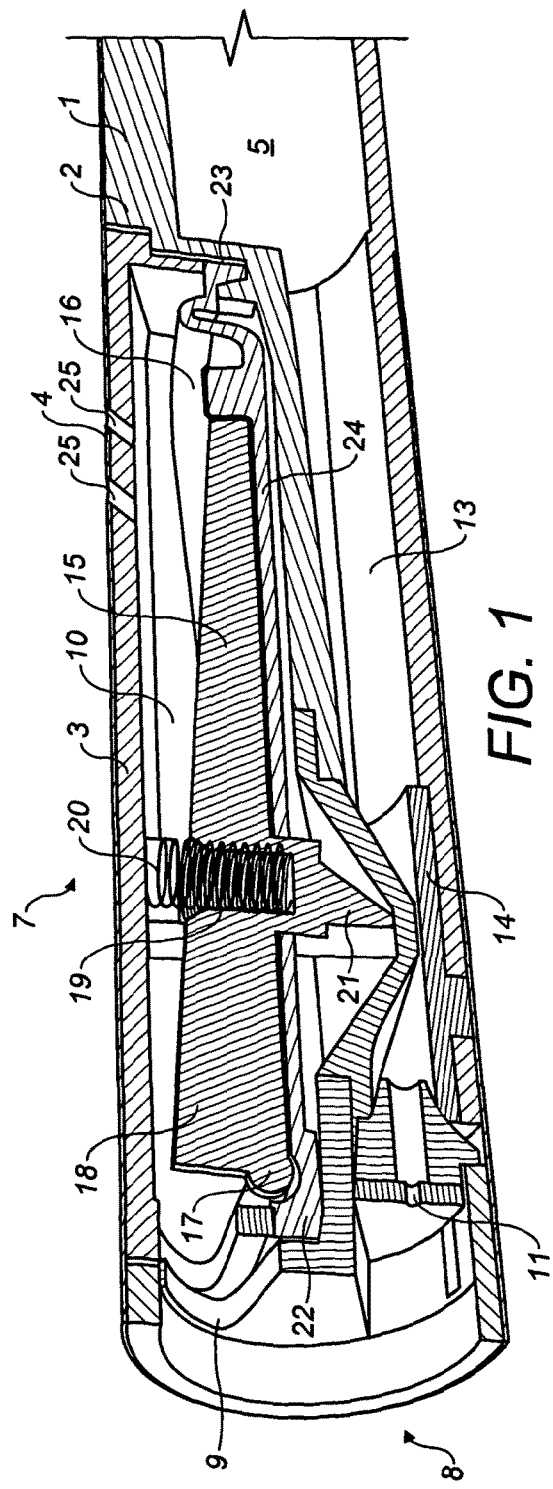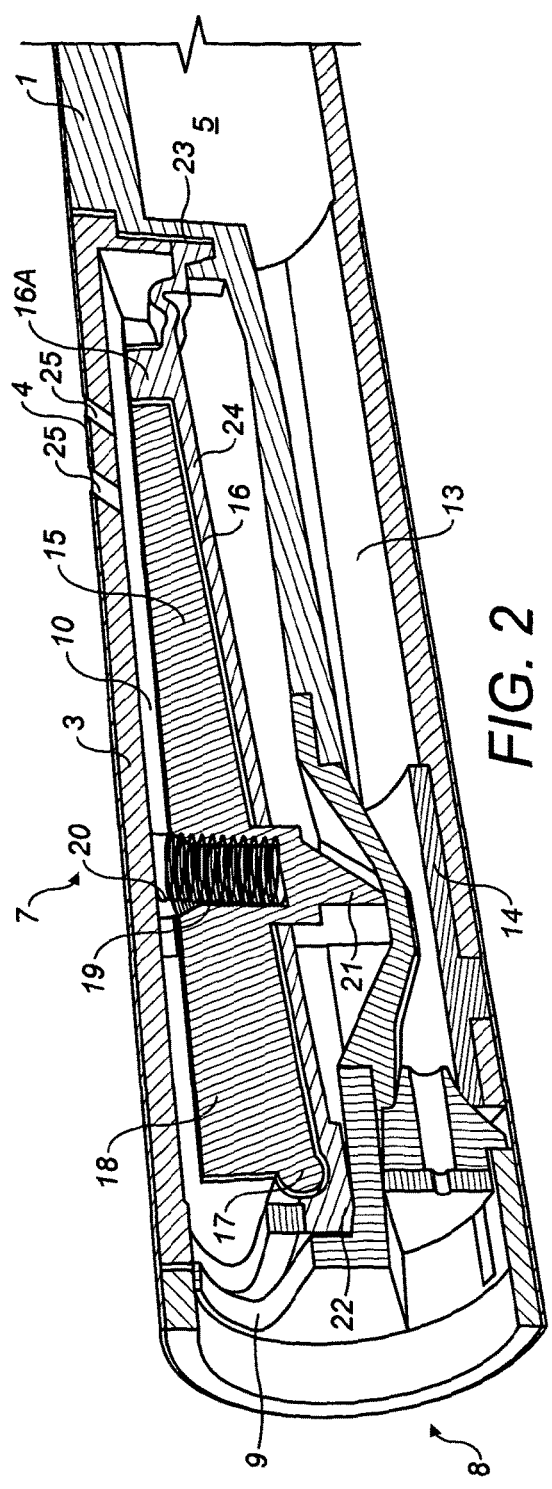

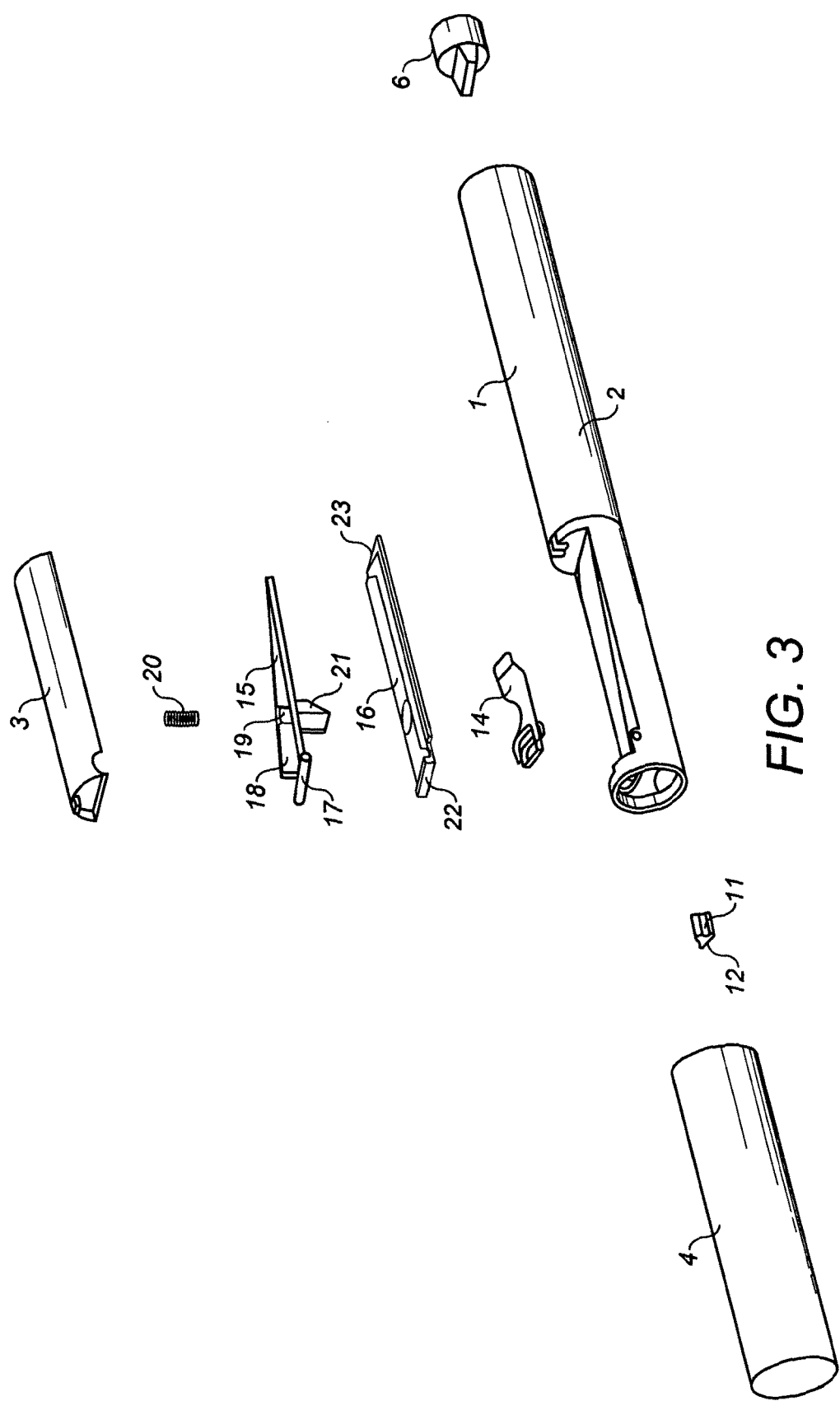

INHALER

The present invention relates to an inhaler.

The invention has been specifically designed for a simulated cigarette device having a generally cigarette-shaped body. However, the invention relates to a development of the outlet valve for such a device which has broader applications in the field of inhalers, for example, medicinal inhalers for oral drug delivery such as asthma inhalers.

In the field of cigarette replacements, there have been a number of proposals to create a simulated cigarette. Such a device has a number of advantages over traditional nicotine replacement therapies such as patches and gum in that they recreate the physical act of smoking which is psychologically important to a smoker, and also are able to deliver nicotine as a dose which more closely replicates the pharmacokinetic effects of a cigarette that persistent smokers desire. Thus, a smoker is able to obtain the "hit" that is familiar from a cigarette, rather than having to deal with the slow release from a patch or gum which does not produce such a hit which leads to unpredictable dosings and poor craving scores and cessation rates.

A simulated cigarette has a reservoir of inhalable composition and an outlet valve which can be trigged, for example, by pushing a button or biting on the end of a cigarette. However, a preferred mechanism for opening the valve is to provide a breath-activated valve as this ensures that the cigarette will only dispense when the user sucks on the device in a manner of a normal cigarette.

U.S. Pat. No. 4,393,884 discloses one such device which has a large resilient "tongue" with a flow path passing through it. This tongue is biased into a first position in which it is out of alignment with the outlet of the cigarette and can be sucked into a second position in which it aligns with the outlet of the cigarette to provide a flow path from the reservoir to the outlet. Such a device is difficult to seal in the first position. It will also require considerable force in order to suck the tongue to the open position against the action of a retaining spring and the relatively large mass of the tongue means that it will be difficult to return to the closed position meaning that dispensing will continue after the suction has been removed.

U.S. Pat. No. 6,889,687 discloses a further example of a simulated cigarette with a breath-activated valve. This discloses a number of examples. One of these has a pair of magnets, one of which is retained by a flexible membrane which allows the magnet to moved apart when suction is applied to a device. This opens up a flow path from the reservoir. However, the mechanism is reasonably complex and has a tortuous flow path which is likely to impede delivery of the composition from the reservoir. A second example is a spring-biased plunger which is moved axially to open up a passageway in a central rod. Such an axially movable plunger is undesirable in practice as it has been found that the level of suction required to overcome the spring biasing force is too high to be usable in practice. Also, the flow path in the open position is out of the rod, into the plunger and back into the rod so that it is again somewhat tortuous. The third example relies on a magnetic interface where the force on which is overcome by a system of vanes which rotate about the axis of the device, thereby moving along a cam surface to pull the magnetic valve element from its seat. Again, this suffers from problems of complexity, lack of control and a tortuous flow path.

U.S. Pat. No. 5,027,808 discloses an inhaler in which suction on a mouthpiece pulls on a flexible diaphragm causing it to be sucked into the inhaler towards the mouthpiece. This, in turn, moves a linkage mechanism which releases a spring-loaded mechanism, the spring providing the force to push against the canister to dispense the material. The linkage mechanism introduces considerable complexity and bulk to the dispensing mechanism. The dispenser does not offer variable control in that it can either be on or off, and it needs to be re-set by the user pushing a push-button.

WO 2009/001082 which is our own earlier application discloses two different breath-activated devices. The first of these has a pair of vane systems rotatable about an axis perpendicular to the main axis of the device to align an orifice with the outlet orifice from the reservoir enabling dispensing. The second of these has a pair of hinged flaps which are sucked down against the action of return springs in order to open the flow path. While this solves some of the problems in that it provides a simple mechanism and an axial flow path, the force required as suction to trigger the device is comparatively large and the user, as a result, can exert less control over the system to release a variable dose, small or large according to the inhalation intake.

The present invention is aimed at providing an improved breath-operated valve for an inhaler and, particularly, a simulated cigarette.

According to the present invention, there is provided an inhaler comprising a reservoir of an inhalable composition;

a housing containing the reservoir and having an outlet end and an opposite end;

a composition flow path for the flow of the composition from the reservoir along the flow path and out of a composition outlet at the outlet end of the housing;

a flexible diaphragm within the housing defining an air flow path from an air inlet to an air outlet at the outlet end of the housing, the diaphragm extending past the air flow inlet towards the opposite end separating the air flow path on one side of the diaphragm from the remainder of the housing on the opposite side of the diaphragm;

a valve element movable with the diaphragm and biased by a biasing force into a position in which it closes the composition flow path;

wherein suction on the outlet end reduces the pressure in the air flow chamber thereby lifting the valve element against the biasing force to open the composition flow path; and wherein the biasing force is arranged to close the composition flow path once the suction ceases.

The use of a diaphragm extending beyond the air flow inlet and defining an air flow path which moves under negative pressure provides a reliable, simple and sensitive valve mechanism.

Further, tests have shown that this arrangement can be configured to require less force to operate by the user than prior art designs giving the user a greater degree of control over the device as well as a quicker response, thereby providing an experience more akin to a conventional cigarette.

Preferably, the composition flow path is a substantially straight path devoid of bends. This provides the most efficient transfer of the composition to the composition outlet.

In order to operate most efficiently, the flexible diaphragm should be particularly flexible in the region adjacent to the air inlet and more rigid along the remainder of its length. This may be achieved simply by making the flexible diaphragm thinner in the region of the air inlet and thicker for the remainder of its length. It may be thicker across its entire width, or may be molded with longitudinally extending ribs.

However, preferably, some additional reinforcement is provided along the length of the diaphragm. This may take the form of internal stiffening ribs, but is preferably a vane which extends along the length of the majority of the flexible diaphragm.

The valve element may be separate from the vane, but is conveniently integral with the vane and can be co-molded to ensure a simple assembly.

The vane may be free at both ends so that it simply translates from one position to the other. However, preferably, the vane is pivotally mounted at the end remote from the air inlet so that it moves between the open and closed positions. This allows the vane to exercise maximum tangential force about the pivot which affects its torque and so increase the responsiveness to the user's breath.

The sensitivity of the device is determined largely by the surface area of the diaphragm (including the vane if present) which is exposed to the air flow path. The membrane therefore preferably extends for at least a quarter and preferably at least a third of the total length of the inhaler.

The movable valve element may be configured in any way in which it can selectively open and close the composition flow path as it is moved by the diaphragm. It may be a magnetic or an electromagnetic device, or may simply have a through orifice which is selectively aligned with the composition flow path. However, preferably, at least a portion of the composition flow path is a deformable tube which is selectively pinched and released by the valve element.

Although a single diaphragm and associated valve element is preferred, the invention could also be performed with a pair of opposed diaphragms and valve elements which move away from one another when suction is applied at the outlet end in order to open the composition flow path.

Preferably, the flexible diaphragm is configured such that the required actuation force is between 2N and 20N, more preferably from 2N to 10N and most preferably substantially 5N.

The total area, in plan, of the flexible diaphragm exposed to the air flow path (including any parts covered by the vane but excluding any parts which are clamped to the surrounding housing) is between 100 mm$^2$ and 500 mm$^2$, more preferably 150 mm$^2$-250 mm$^2$ and most preferably substantially 200 mm. This is effectively the area over which the reduced pressure acts on the diaphragm, including, if present, the vane. Providing a reasonably large area reduces the suction force required to open the valve.

The vane preferably has a height of 5 mm-10 mm, most preferably 8 mm and a length of 10 mm-40 mm, most preferably 25 mm.

At its narrowest point the thickness of the diaphragm may be preferably less than 1 mm, more preferably between 0.1 mm and 0.4 mm and most preferably 0.1 mm. The relative rigidity and flexibility of the diaphragm also needs to be calibrated in order to equate the pressure drop and resistance of the device to that of tobacco smoking.

Preferably the material with have a Shore rating of 20-80 A shore, most preferably 30-40 A.

The inhaler may be a drug delivery inhaler for any inhalable pharmaceutical composition. However, the inhaler is preferably a simulated cigarette device having a generally cigarette-shaped body. In this case, the inhalable composition preferably includes nicotine or a nicotine derivative or salt thereof. On the other hand, it may be a simulated cigarette which replicates the physical act of smoking without requiring nicotine in the composition. Alternatively, the composition may include patient controlled analgesics, anti-inflammatory, anti-spasmodics, bronchodilators, centicosteroids, retro-virals or opiates.

Examples of inhalers in accordance with the present invention will now be described with reference to the accompanying drawings, in which:

FIG. 1 is a section through a perspective view of a first inhaler in a closed position;

FIG. 2 is a similar view in the open position; and

FIG. 3 is an exploded perspective view of the inhaler of FIGS. 1 and 2.

The present invention relates to an improvement of the outlet valve for a breath-activated cigarette and only this aspect of the invention will be specifically described here. For details of the construction of the remainder of the cigarette device and its refill mechanism, reference is made to WO 2009/001078.

The first example of an inhaler in accordance with the present invention is shown in FIGS. 1 to 3.

The device has a housing 1 made up of a main chassis 2 and a closure element 3 as shown in FIG. 1. This is held in place by label 4. Within the housing, there is a reservoir 5 containing the inhalable composition. This is preferably pressurised but could also work with a non-pressurised reservoir in combination with a Venturi nozzle to generate an enhanced suction force on the reservoir, or a non-pressurised reservoir containing a substance that is prone to evaporating at room temperature. It may be refillable as described in WO 2009/001082 through the filling valve 6, or the device may be a single use device, or may be arranged so that the reservoir 5 is a replaceable component.

The breath-activated valve 7 is positioned between an outlet end 8 and the reservoir 5. The breath-activated valve is arranged so that, when a user sucks on the outlet end 8, the breath-activated valve 7 opens to allow the inhalable composition from the reservoir 5 to be inhaled.

The housing at the outlet end has two orifices. The first of these is the suction orifice 9 which communicates with a chamber 10 as will be described in greater detail below and the second is an outlet orifice 11 from which the inhalable composition dispensed is also described in more detail below. As is apparent from FIG. 3, the outlet orifice 11 is provided on a separate component 12.

An outlet path 13 is defined between the reservoir 5 and outlet orifice 11.

A portion of the outlet path 13 is provided by deformable tubular element 14. This tubular element is moved between the closed position shown in FIG. 1 and the open position shown in FIG. 2 by a mechanism which will now be described.

This mechanism comprises a pivotally mounted vane 15 and a membrane 16. The membrane is preferably injection molded for example a TPU or TPE material e.g Kraiburg Pharmaceutical grade TPE, or a mediprene, Santoprene or Neoprene. The pivotally mounted vane has a pivot 17 at the end closest to the outlet end 8 and a central reinforcing rib 18 running along its length and tapering away from the outlet end. Alternatively, there may be two or more spaced ribs. At around the midpoint, the vane 15 is provided with a recess 19 for receiving a spring 20 which biases it into the closed position shown in FIG. 1. Below the recess 19 is a jaw 21 having a triangular cross-section which is configured to apply the force provided from the vane 15 to the deformable tube 14 over a narrow area. The vane 15 is supported by the diaphragm 16 by virtue of the fitting of the jaw 21 through an aperture in the diaphragm and a boss 16A on the diaphragm fitting into an aperture on the vane 15. The diaphragm 16 is sealed to the housing at its ends 22, 23. This seals off the chamber 10 other than to the suction orifice 9. At the end 23, the diaphragm 16 is corrugated to accommodate the movement of that end between the open and closed positions.

The underside 24 of the membrane 16 is open to atmospheric pressure as a leakage path exists through the housing 1 which is not shown in the drawings as it extends around the outlet path 1 and is therefore not shown in the plane of FIGS. 1 and 2.

When a user sucks on the outlet end 8 with the device in the configuration shown in FIG. 1, air is sucked into the chamber 10 via inlet orifices 25 and out of suction orifice 9 thereby lowering the pressure in this chamber with respect to the pressure beneath the diaphragm 16. The pressure differential created on the diaphragm 16 is sufficient to close the flow path. For example, it can lift the vane 15 against the action of the spring 20 to the position shown in FIG. 2. This deforms the diaphragm into the configuration shown in FIG. 2 and lifting the jaw 21 to allow the deformable tube to open, thereby allowing the inhalable composition from the reservoir 5 along outlet path 13 through the deformable tube 14 and out through the outlet orifice 11. The degree of suction applied by the user will determine the extent to which the vane 15 moves and therefore the amount of composition that the user receives. As soon as a user stops sucking, atmospheric pressure will return to the chamber 10 via the suction orifice 9 and the spring 20 will return the vane to the FIG. 1 position thereby pinching the tube 14 closed.

The invention claimed is:

1. An inhaler comprising:
   a reservoir for holding a plurality of doses of a composition to be inhaled;
   a housing containing the reservoir and having an outlet end where each dose of the composition exits the inhaler and an opposite end;
   a composition flow path extending from the reservoir to the outlet end of the housing along which the composition flows from the reservoir along the flow path and out of a composition orifice towards the outlet end of the housing;
   a flexible diaphragm which does not form part of the composition flow path defining a suction chamber on one side of the diaphragm, the suction chamber extending from an air outlet proximate to the outlet end of the housing, and terminating part way along the housing such that the diaphragm separates the suction chamber on one side of the diaphragm from the remainder of the housing on the opposite side of the diaphragm;
   a valve element movable with the diaphragm and biased by a biasing force into a first position in which it closes the composition flow path at a position between the reservoir and the composition orifice;
   wherein suction on the outlet end reduces the pressure in the suction chamber thereby moving the valve element against the biasing force to a second position to open the composition flow path so that a single dose out of the plurality of doses of the composition held in the reservoir can flow uninterrupted from the reservoir through the composition orifice and out of the outlet end; and
   wherein the said biasing force is arranged to return the valve element to the first position to close the composition flow path to stop the flow of the composition from the reservoir through the composition orifice once the single dose is complete and the suction ceases.

2. The inhaler according to claim 1, further comprising a vane which extends along a length of a majority of the flexible diaphragm.

3. The inhaler according to claim 2, wherein the valve element is integral with the vane.

4. The inhaler according to claim 1, wherein the diaphragm extends for at least a quarter of a total length of the inhaler.

5. The inhaler according to claim 1, the diaphragm extends for at least a third of a total length of the inhaler.

6. The inhaler according to claim 1, wherein at least a portion of the composition flow path is a deformable tube which is selectively pinched and released by the valve element in the first and second positions, respectively.

7. The inhaler according to claim 1, wherein the flexible diaphragm is configured such that a required actuation force is between 7N and 10N.

8. The inhaler according to claim 1, wherein the flexible diaphragm is configured such that a required actuation force is substantially 5N.

9. The inhaler according to claim 1, wherein the flexible diaphragm has a hardness of 30-40 A on the Shore A scale.

10. The inhaler according to claim 1, wherein the inhaler is a simulated cigarette.

11. An inhaler comprising:
    a reservoir for holding a composition to be inhaled;
    a housing containing the reservoir and having an outlet end where composition exits the inhaler and an opposite end;
    a composition flow path extending from the reservoir to the outlet end of the housing along which the composition flows from the reservoir along the flow path and out of a composition orifice towards the outlet end of the housing;
    a flexible diaphragm which does not form part of the composition flow path defining a suction chamber on one side of the diaphragm, the suction chamber extending from an air outlet proximate to the outlet end of the housing, and terminating part way along the housing such that the diaphragm separates the suction chamber on one side of the diaphragm from the remainder of the housing on the opposite side of the diaphragm;
    a valve element movable with the diaphragm and biased by a biasing force into a first position in which it closes the composition flow path at a position between the reservoir and the composition orifice;
    wherein suction on the outlet end reduces the pressure in the suction chamber thereby moving the valve element against the biasing force to a second position to open the composition flow path so that the composition can flow uninterrupted from the reservoir through the composition orifice and out of the outlet end;
    wherein the said biasing force is arranged to return the valve element to the first position to close the composition flow path to stop the flow of the composition from the reservoir through the composition orifice once the suction ceases; and
    wherein the flexible diaphragm is configured such that a required actuation force is between 2N and 20N.

12. An inhaler comprising:
    a reservoir for holding a composition to be inhaled;
    a housing containing the reservoir and having an outlet end where composition exits the inhaler and an opposite end;
    a composition flow path extending from the reservoir to the outlet end of the housing along which the composition flows from the reservoir along the flow path and out of a composition orifice towards the outlet end of the housing;

a flexible diaphragm which does not form part of the composition flow path defining a suction chamber on one side of the diaphragm, the suction chamber extending from an air outlet proximate to the outlet end of the housing, and terminating part way along the housing such that the diaphragm separates the suction chamber on one side of the diaphragm from the remainder of the housing on the opposite side of the diaphragm;

a valve element movable with the diaphragm and biased by a biasing force into a first position in which it closes the composition flow path at a position between the reservoir and the composition orifice;

wherein suction on the outlet end reduces the pressure in the suction chamber thereby moving the valve element against the biasing force to a second position to open the composition flow path so that the composition can flow uninterrupted from the reservoir through the composition orifice and out of the outlet end;

wherein the said biasing force is arranged to return the valve element to the first position to close the composition flow path to stop the flow of the composition from the reservoir through the composition orifice once the suction ceases; and wherein the flexible diaphragm has a hardness of 20-80 A on the Shore A scale.

13. An inhaler comprising:

a reservoir for holding a composition to be inhaled;

a housing containing the reservoir and having an outlet end where composition exits the inhaler and an opposite end;

a composition flow path extending from the reservoir to the outlet end of the housing along which the composition flows from the reservoir along the flow path and out of a composition orifice towards the outlet end of the housing;

a flexible diaphragm which does not form part of the composition flow path defining a suction chamber on one side of the diaphragm, the suction chamber extending from an air outlet proximate to the outlet end of the housing, and terminating part way along the housing such that the diaphragm separates the suction chamber on one side of the diaphragm from the remainder of the housing on the opposite side of the diaphragm;

a valve element movable with the diaphragm and biased by a biasing force into a first position in which it closes the composition flow path at a position between the reservoir and the composition orifice;

a vane which extends along a length of a majority of the flexible diaphragm;

wherein suction on the outlet end reduces the pressure in the suction chamber thereby moving the valve element against the biasing force to a second position to open the composition flow path so that the composition can flow uninterrupted from the reservoir through the composition orifice and out of the outlet end;

wherein the said biasing force is arranged to return the valve element to the first position to close the composition flow path to stop the flow of the composition from the reservoir through the composition orifice once the suction ceases; and wherein a total area, in plan, of the flexible diaphragm exposed to the suction chamber including any parts covered by the vane but excluding any parts which are clamped to the housing is between 100 $mm^2$ and 500 $mm^2$.

14. The inhaler according to claim 13, wherein a total area, in plan, of the flexible diaphragm exposed to the suction chamber including any parts covered by the vane but excluding any parts which are clamped to the housing is between 150 $mm^2$ and 250 $mm^2$.

15. The inhaler according to claim 14, wherein a total area, in plan, of the flexible diaphragm exposed to the suction chamber including any parts covered by the vane but excluding any parts which are clamped to the housing is substantially 200 $mm^2$.

* * * * *